(12) United States Patent
Fleenor et al.

(10) Patent No.: US 6,554,845 B1
(45) Date of Patent: Apr. 29, 2003

(54) SUTURING APPARATUS AND METHOD

(75) Inventors: Richard P. Fleenor, Englewood, CO (US); Robert L. Bromley, Littleton, CO (US)

(73) Assignee: PARÉ Surgical, Inc., Englewood, CO (US)

( * ) Notice: Subject to any disclaimer, the term of this patent is extended or adjusted under 35 U.S.C. 154(b) by 202 days.

(21) Appl. No.: 09/662,936

(22) Filed: Sep. 15, 2000

(51) Int. Cl.[7] .............................................. A61B 17/00

(52) U.S. Cl. ...................................... 606/148; 606/139

(58) Field of Search ................................ 606/139, 144, 606/145, 146, 148, 222, 223, 228, 232; 128/898

(56) References Cited

U.S. PATENT DOCUMENTS

| | | | |
|---|---|---|---|
| 5,037,433 A | | 8/1991 | Wilk et al. |
| 5,318,578 A | * | 6/1994 | Hasson ........................ 606/139 |
| 5,501,692 A | | 3/1996 | Riza |
| 5,527,323 A | * | 6/1996 | Jervis et al. ................. 606/148 |
| 5,584,861 A | | 12/1996 | Swain et al. |
| 5,643,292 A | * | 7/1997 | Hart ............................ 606/139 |
| 5,681,331 A | * | 10/1997 | de la Torre et al. ......... 606/148 |
| 5,716,368 A | * | 2/1998 | de la Torre et al. ......... 606/148 |
| 5,741,280 A | * | 4/1998 | Fleenor ....................... 606/148 |
| 5,755,728 A | * | 5/1998 | Maki ........................... 606/145 |
| 5,755,730 A | * | 5/1998 | Swain et al. ................. 606/148 |
| 5,792,153 A | | 8/1998 | Swain et al. |
| 5,814,068 A | * | 9/1998 | Koike et al. ................. 606/228 |
| 5,908,429 A | * | 6/1999 | Yoon ........................... 606/144 |
| 6,010,515 A | * | 1/2000 | Swain et al. ................. 606/148 |
| 6,221,084 B1 | * | 4/2001 | Fleenor et al. .............. 606/148 |
| 6,245,081 B1 | * | 6/2001 | Bowman et al. ............ 606/148 |

OTHER PUBLICATIONS

Sabine Cecile Fischer, Klaus Roth, Alberto Arezzo, Heike Raestrup, Marc Oliver Schurr, Gerhard Fritz Buess; "Comparative Study of the Use of a Suturing System and Titanium Clips", Surgical Technology International IX; 5 pages.
Brochure Entitled "Successful Uses in Approximation Ligation and Fixation Using the Quik–Stitch Endoscopic Suturing System".
Brochure Entitled "Secure Suturing With a 5mm Delivery System and a Pre–Tied Roeder Knot", 1 Page.
Advertisement Entitled "Quik–Stitch Sails Ahead With Unparalleled Advantages", 1 Page.
Product Information Entitled "Bard Endoscopic Suturing System: Suture/Plication Overview", 8 Pages.

* cited by examiner

*Primary Examiner*—Gloria M. Hale
(74) *Attorney, Agent, or Firm*—Marsh Fischmann & Breyfogle LLP

(57) ABSTRACT

In one embodiment of a suturing apparatus a needle member is provided with a suture material having a pre-tied knot disposed about a distal end of the needle member. The suturing apparatus further includes a first member, wherein the first member and needle member are disposed to permit selective relative movement therebetween. Upon such movement, the first member is positionable to engage and position the pre-tied knot beyond the distal end of the needle member. Such an arrangement facilitates internal suture stitching and knot placement. An advanceable/retractable grasping member may be advantageously included in the suturing apparatus for selectively retaining/releasing an end of the suture material. The grasping member may be defined by a spring-loaded hoop member that may be selectively deployed out of a hollow piercing tip comprising the needle member. In the deployed state the grasping member may be positioned about the end of the suture material (e.g., after the suture material has been pulled through a surgical site by the needle member). Thereafter, retraction of the hoop member into the hollow piercing tip will cause the hoop member to collapse and grasp the end of the suture material for subsequent suturing steps.

69 Claims, 11 Drawing Sheets

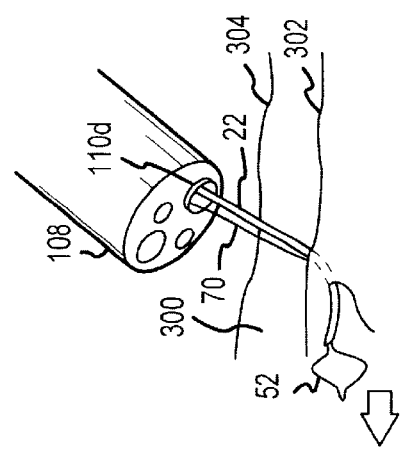
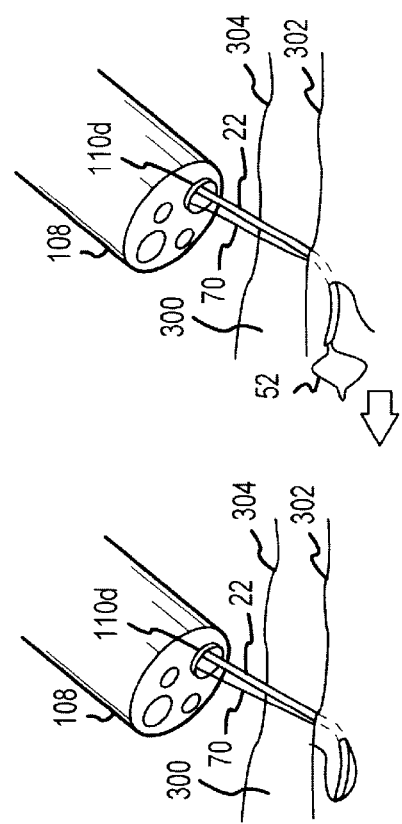
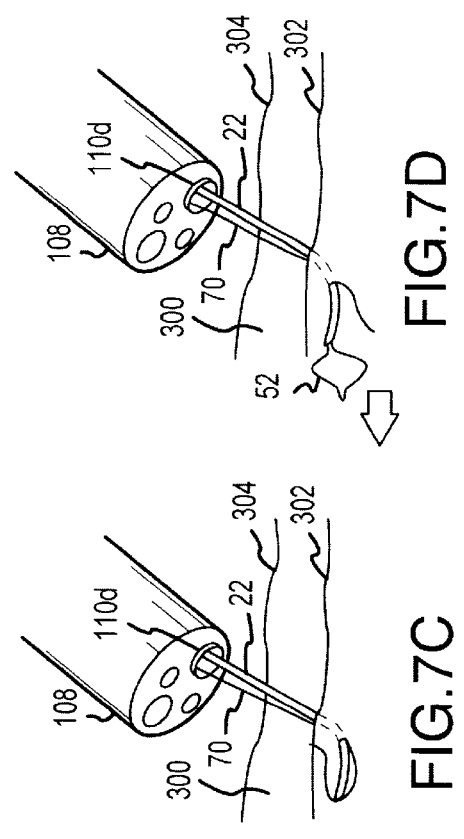
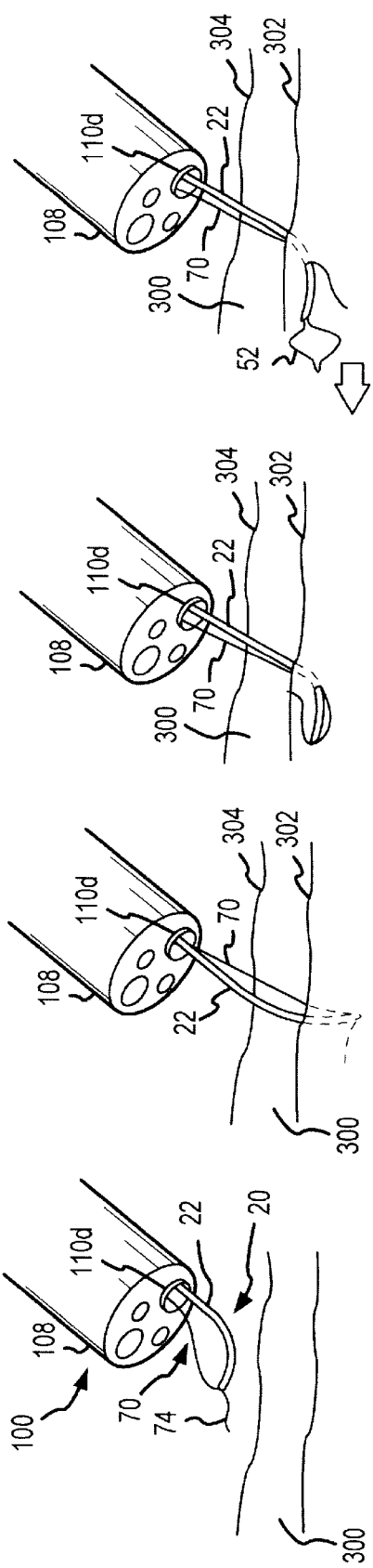
FIG.7A  FIG.7B  FIG.7C  FIG.7D
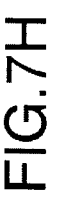
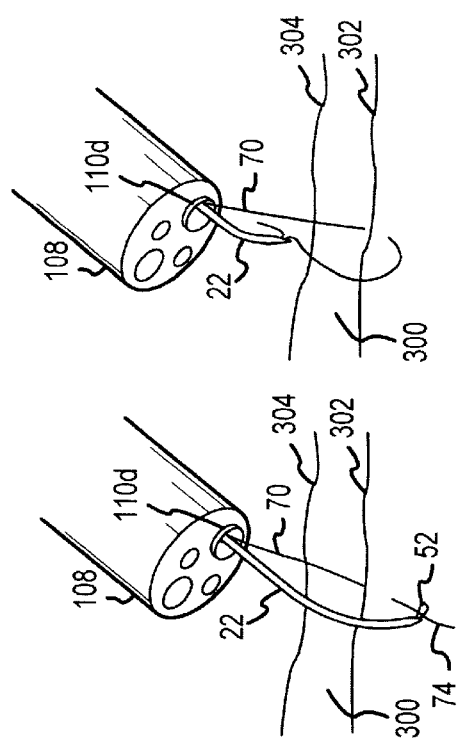
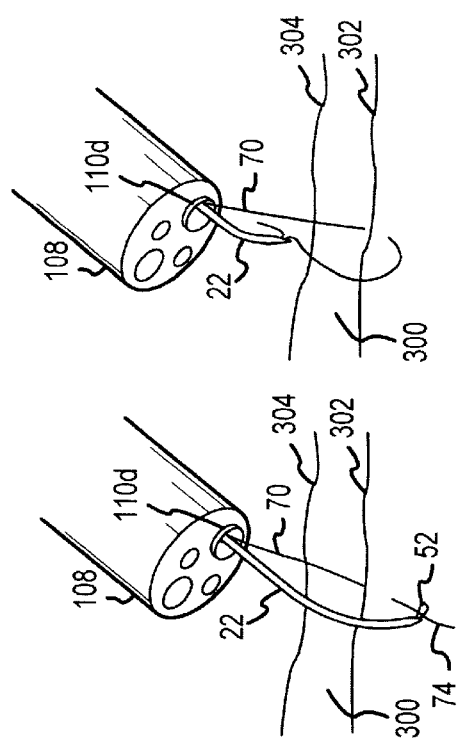
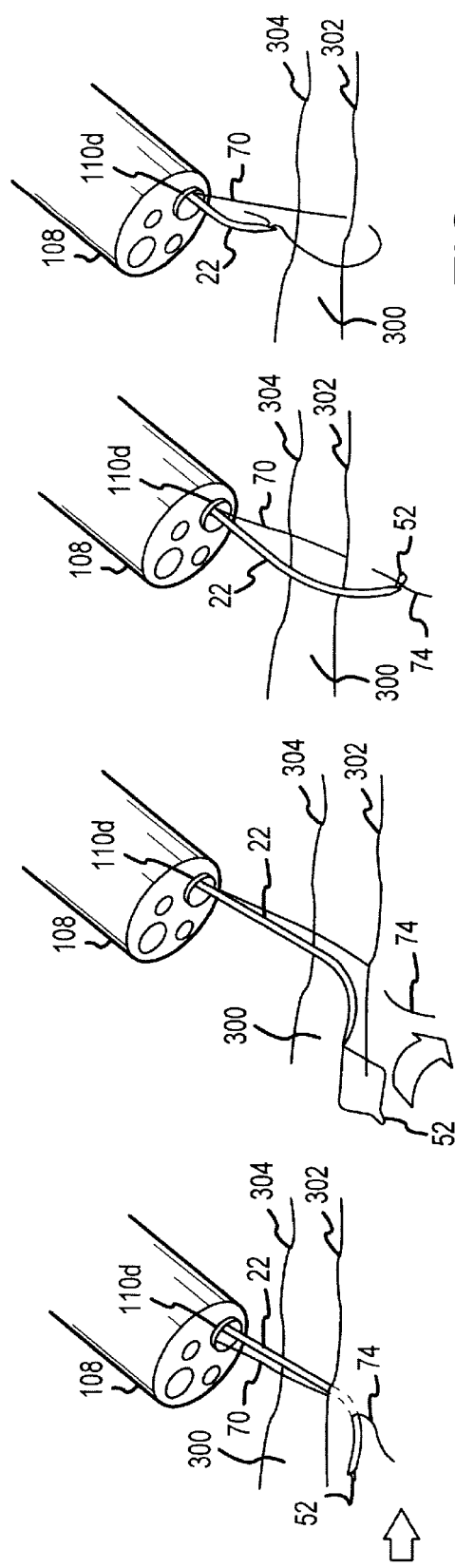
FIG.7E  FIG.7F  FIG.7G  FIG.7H

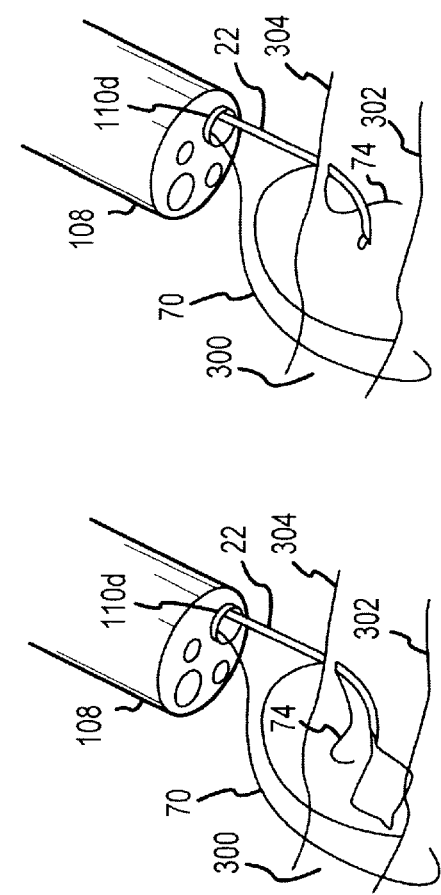
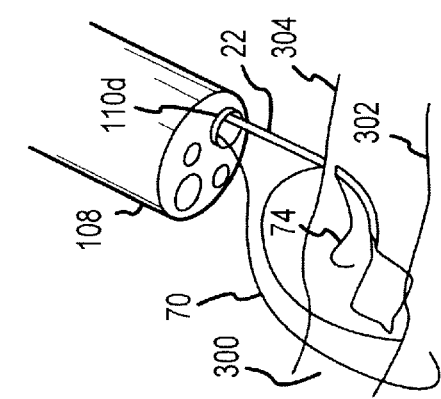
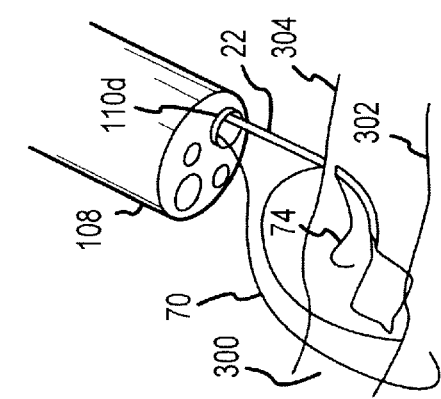
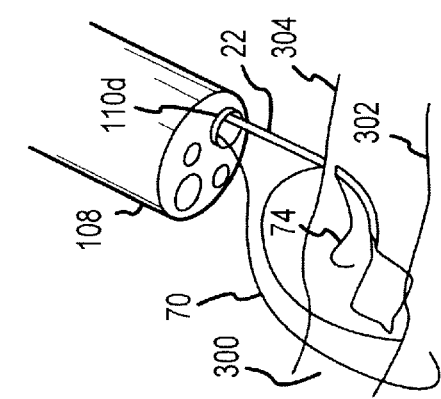
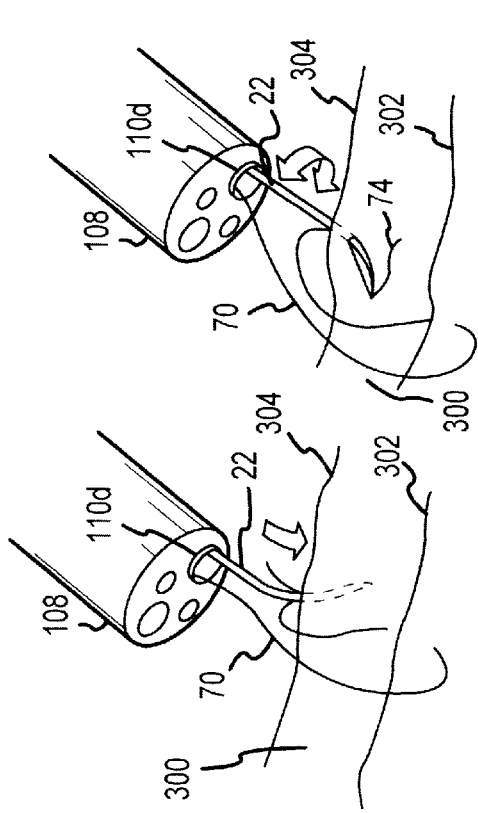
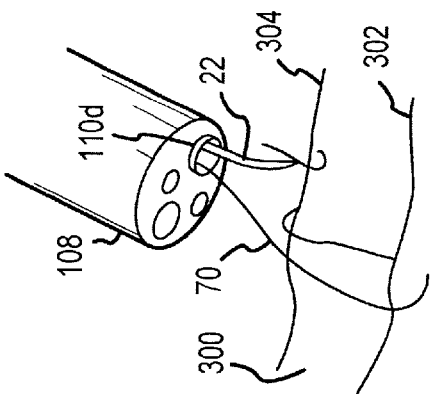
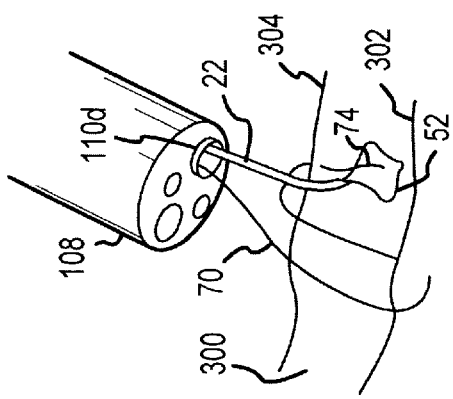

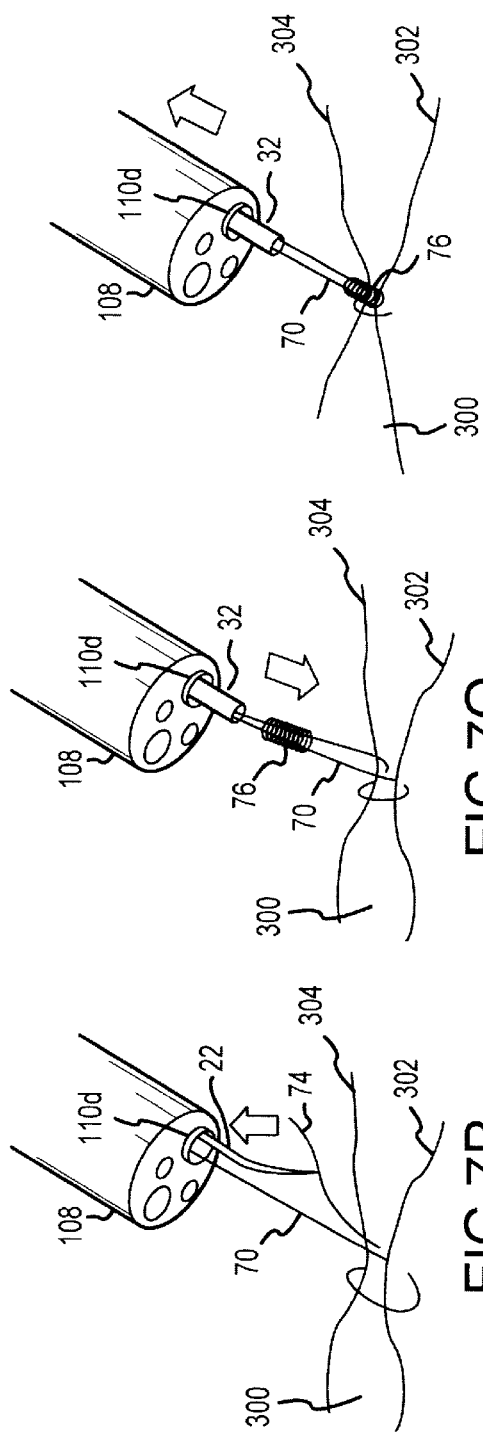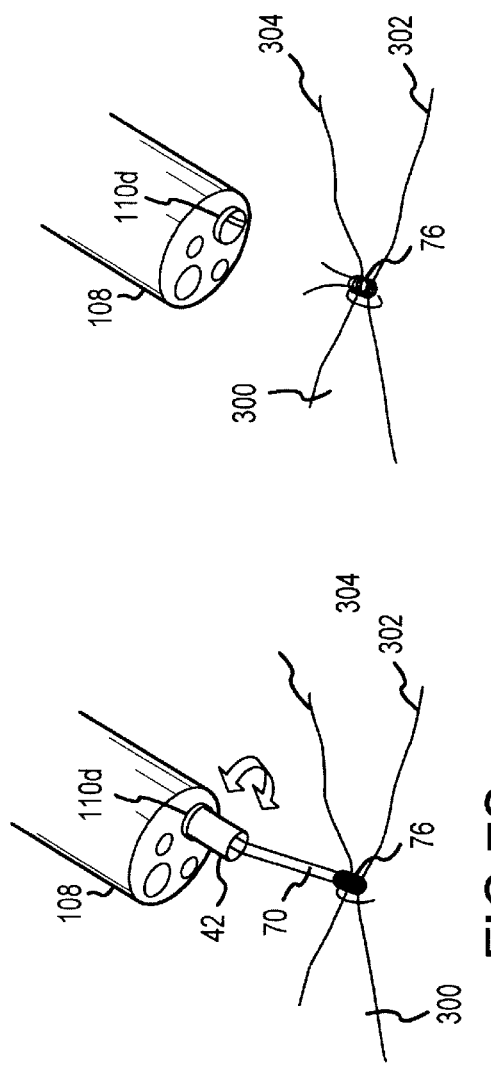

SUTURING APPARATUS AND METHOD

FIELD OF THE INVENTION

The present invention relates to the field of minimally-invasive internal surgery, and more particularly, to methods and apparatus for suturing within a patient body via the manipulation of devices external to a patient body.

BACKGROUND OF THE INVENTION

Minimally invasive internal surgery procedures are ever-increasing. Such procedures typically entail the insertion of a tubular member into a patient body and the passage of various devices through the tubular member to access a tissue site of interest. In laparoscopic procedures, a plurality of tubular members, e.g., trocars, may be inserted through offset incisions and advanced proximal to the tissue site of interest. The tubular members utilized are relatively rigid and of a diameter sufficient to facilitate the passage of a wide variety of devices therethrough, including for example the passage of gas inflation conduits, electrosurgical devices, imaging apparatus and suturing devices. As may be appreciated, laparoscopic surgical procedures include those directed to fundoplications, myomectomies, splenectomies, herniorrhaphies and cholecystectomies.

In endoscopic procedures, a single tubular member is typically inserted through a bodily orifice to provide instrumentation access therethrough to an internal tissue site, e.g., through the mouth or anus to access a hollow organ. Given such access points and associated bodily canals, the tubular members utilized in endoscopic applications are necessarily of flexible construction and may be of significant length. Such considerations present particular challenges in the design and development of endoscopic surgical apparatus and techniques. To date, endoscopic procedures have been largely limited to gasdroesophergeal (GERD) and biopsy applications. However, it is believed that new surgical devices and procedures may be developed that facilitate increased endoscopic applications involving the ligating, proximating and suturing of tissue in the stomach and colon.

Common to both laparoscopic and endoscopic surgical procedures is the need to effectively suture an internal tissue site of interest. Such suturing entails the passage of a suture material into and back out of the tissue at least once, and most typically a plurality of times, followed by the provision and tightening of a knot adjacent to the sutured tissue. As may be appreciated, the completion of suturing procedures in laparoscopic and endoscopic applications can present a challenging and sometimes tedious task for surgical personnel. For example, such suturing procedures may involve difficult manipulation of an external device to cause an internally located needle to pass entirely through tissue at a surgical site to effect suture stitching. Further, in some approaches, the provision of a suture knot at a sutured site may require the time-consuming removal and reinsertion of the entire suturing apparatus and access tubing therefor.

SUMMARY OF THE INVENTION

In view of the foregoing, a broad objective of the present invention is to provide methods and apparatus for internal suturing that are relatively simple to employ yet highly effective.

An additional objective of the present invention is to provide for internal suturing in a manner that reduces componentry cost and complexity.

Another objective of the present invention is to provide for internal suturing in a manner that reduces the overall time required for suturing in a given procedure.

Yet a further objective of the present invention is to provide for internal suturing in a manner that accommodates a wide variety of applications.

An additional objective of the present invention is to provide for internal suturing in a manner that allows for substantially continuous imaging of the entire suturing process.

One or more of the above-noted objectives and additional advantages are realized in a suturing apparatus that comprises a needle member having a distal end portion and a suture material having a pre-tied knot (e.g., a Roeder knot) initially disposed about the distal end of the needle member. As will be appreciated, the needle member may be of a length sufficient to permit external manipulation of a proximal end so as to "thread" the suture material through tissue at a surgical site.

In one aspect of the invention, the apparatus further includes a first member disposed for selective relative movement between the first member and the needle member. Upon such relative movement, the first member is positionable to engage the suture material and thereby position the pre-tied knot beyond the distal end of the needle member, e.g., for subsequent tightening at a surgical site. By virtue of this arrangement, the provision of a suture knot at a sutured site may be accurately and readily accomplished.

The distal end of the needle member may comprise piercing tip. By way of example, such piercing tip may be of a straight or arcuate configuration. Correspondingly, the needle member may be provided so that rotation of a proximal end portion thereof effects substantially co-rotational movement of the piercing tip through a corresponding arc. As will be appreciated, such co-rotational movement facilitates the desired passage, or stitching, of the piercing tip of the member needle into and back out of tissue at a surgical site during suturing procedures. In this regard, it may be preferable to provide a needle member having a torsional strength of at least about 0.02 in. lb. and having buckle strength of at least about 0.2 psi from the distal end to a proximal end thereof.

To facilitate use in endoscopic applications, the needle member may be elongated, with a maximum cross-sectional width, or diameter, of about 0.10 inches. Additionally, for such applications the elongated needle member may preferably comprise a resilient material that permits a degree of flexural curvature along the length thereof. By way of example, the elongated needle member may comprise a material selected from a group consisting of nickel, titanium or nickel titanium alloys, stainless, spring or surgical steel, or flexible plastic.

The inventive apparatus may further comprise a second member having a distal end adapted for cutting the suture material, wherein the second member and at least one of the first member and the needle member are disposed to permit selective relative movement therebetween. More particularly, the second member may be disposed for selective advancement/retraction relative to each of the first member and the needle member. Such an arrangement facilities selective positioning of the second member in a forward position for cutting the suture material, e.g., after tissue has been stitched and a pre-tied knot has been placed/tightened at a given surgical site.

In another aspect of the present invention, a suturing apparatus is provided comprising a needle and suture material having one end anchored near a distal end of the suture needle. Again, the apparatus may be designed so that the needle may be externally manipulated to thread the suture material through tissue at an internal surgical site. The suturing apparatus also includes a grasping member, wherein the needle and grasping member are disposed to permit selective relative movement therebetween. Upon such selective relative movement the grasping member is positionable beyond a distal end of the needle for selectively grasping and/or releasing the suture material, e.g., after threading of the suture material through tissue at a surgical site.

In conjunction with this aspect of the invention, the grasping member may be positioned through at least a portion of the needle, e.g. a hollow piercing tip at the distal end of the needle, and adapted to telescope therebeyond upon selective relative movement therebetween. Further, the grasping member may comprise a spring-loaded portion, (e.g., the grasping member may be shaped to exhibit a spring-loaded behavior), wherein the spring-loaded portion collapses to a non-deployed state upon positioning within a hollow piercing tip of the needle and automatically springs open to a deployed state upon positioning beyond the distal end of the needle. In one embodiment, the spring-loaded portion of the grasping member may be of a hoop-like configuration for selective positioning about an end portion of suture material in a deployed state and for capturing the end portion therethrough in a non-deployed state (e.g., when retracted within the hollow piercing tip of the needle).

In one arrangement implementing various inventive aspects, a suturing apparatus is provided which includes a grasping member, a needle member, a knot positioning member and a suture cutting member, each of which extend in a parallel fashion from a distal end to a proximal end of the suturing apparatus. For example, such members may be disposed in a concentric manner, e.g., wherein the grasping member is located through the needle member, the needle member is positioned through the knot positioning member and the knot positioning member extends through the suture cutting member. In turn, adjacent ones of said members may be disposed to allow for selective advancement/retraction and/or rotation relative to one another via the manipulation of corresponding handles provided at their respective proximal ends. As will be appreciated, in use of the suturing apparatus, the proximal handles may be interconnected for separate manipulation outside a patient body to effect a desired suturing procedure at an internal tissue site adjacent to distal ends of the corresponding grasping, needle, knot positioning, and suture cutting members.

A suturing apparatus having one or more features as described above is particularly well-suited for system applications. In this regard, and in yet another aspect of the present invention, an inventive suturing system is provided that includes a tubular member adapted for insertion into a patient body, an imaging device positioned through the tubular member for acquiring images within an image view range at the distal end of the tubular member, and a suturing apparatus positioned through an accessory part of the tube member for suturing adjacent to the distal end of the tubular member. The suturing apparatus includes a suture needle that is selectively advanceable/retractable within the image view range of the imaging device.

In conjunction with this aspect of the invention, the suturing apparatus may include a suture material having a pre-tied knot disposed about the suture needle. The suturing apparatus may further comprise a first member. The suture needle and first outer member may be disposed to permit selective relative movement therebetween, wherein upon such selective relative movement the first member is positionable to dispose the pre-tied knot beyond a distal end of the suture needle for selective advancement and tightening at a surgical site within the image view range of the imaging device.

To facilitate real-time viewing of the suturing process, a display device may be included within the system to display the acquired images. As will be appreciated, such display device may be advantageously positioned for observation by a user contemporaneous with the user's manipulation of the suturing apparatus. In the latter regard, the suturing apparatus may further include additional features as noted hereinabove.

In yet a further aspect of the present invention, one or more inventive methods for internal suturing are provided. In one aspect, an inventive suturing method provides for the retention of an end portion of a suture material at a distal end of a suture needle and the advancement of a limited portion of the suture needle through a patient tissue site, wherein the end portion of suture material is pulled through the patient tissue site by the suture needle. Thereafter, the end portion of the suture material may be selectively released by the distal end of the suture needle and the limited portion of the suture needle may be withdrawn from the patient tissue site, thereby leaving the end portion of the suture material protruding from the tissue site. In turn, the protruding end portion may then be grasped and a pre-tied knot portion of the suture material may be positioned about the grasped end portion. As may be appreciated, such methodology avoids the need to pass a needle completely through a tissue site in order to complete a stitching process. Rather, in the described method, a suture needle may be utilized one or more times to pull the end of a suture material through a tissue site, with the needle being withdrawn back through the tissue site after each occurrence.

In conjunction with the inventive method, the retention of suture material at a distal end of a suture needle may be accomplished by grasping the end portion of the suture material and pulling the grasped end portion into a hollow portion (e.g., a hollow piercing tip) comprising the distal end of the suture needle. Subsequently, the grasped end portion may be released by advancing the grasped end portion back out of the hollow portion of the needle.

In further relation to the inventive method, positioning of the pre-tied knot portion may be achieved by advancing the pre-tied knot relative to the grasped end portion of the suture material so as to tighten the pre-tied knot portion adjacent to the tissue site. In conjunction with such positioning, the grasped end portion of the suture material may be pulled into a hollow portion at the distal end of the suture needle. After knot tightening, the suture material may be selectively cut, e.g., via selective contact with a cutting surface.

Additional aspects and advantages of the present invention will become apparent upon further consideration of the description that follows.

BRIEF DESCRIPTION OF THE DRAWINGS

FIGS. 7A–7T illustrate steps in the use of the embodiment of FIG. 1B in the system of FIGS. 6A–6C.

DETAILED DESCRIPTION

FIGS. 1A, 2A, 3A and FIGS. 1B, 2B and 2C illustrate two embodiments of a suturing apparatus (10) particularly adapted for endoscopic use. As will be appreciated, numerous other embodiments comprising one or more aspects of the present invention may be constructed, including for example embodiments particularly directed to laparoscopic applications.

Figure 1A:
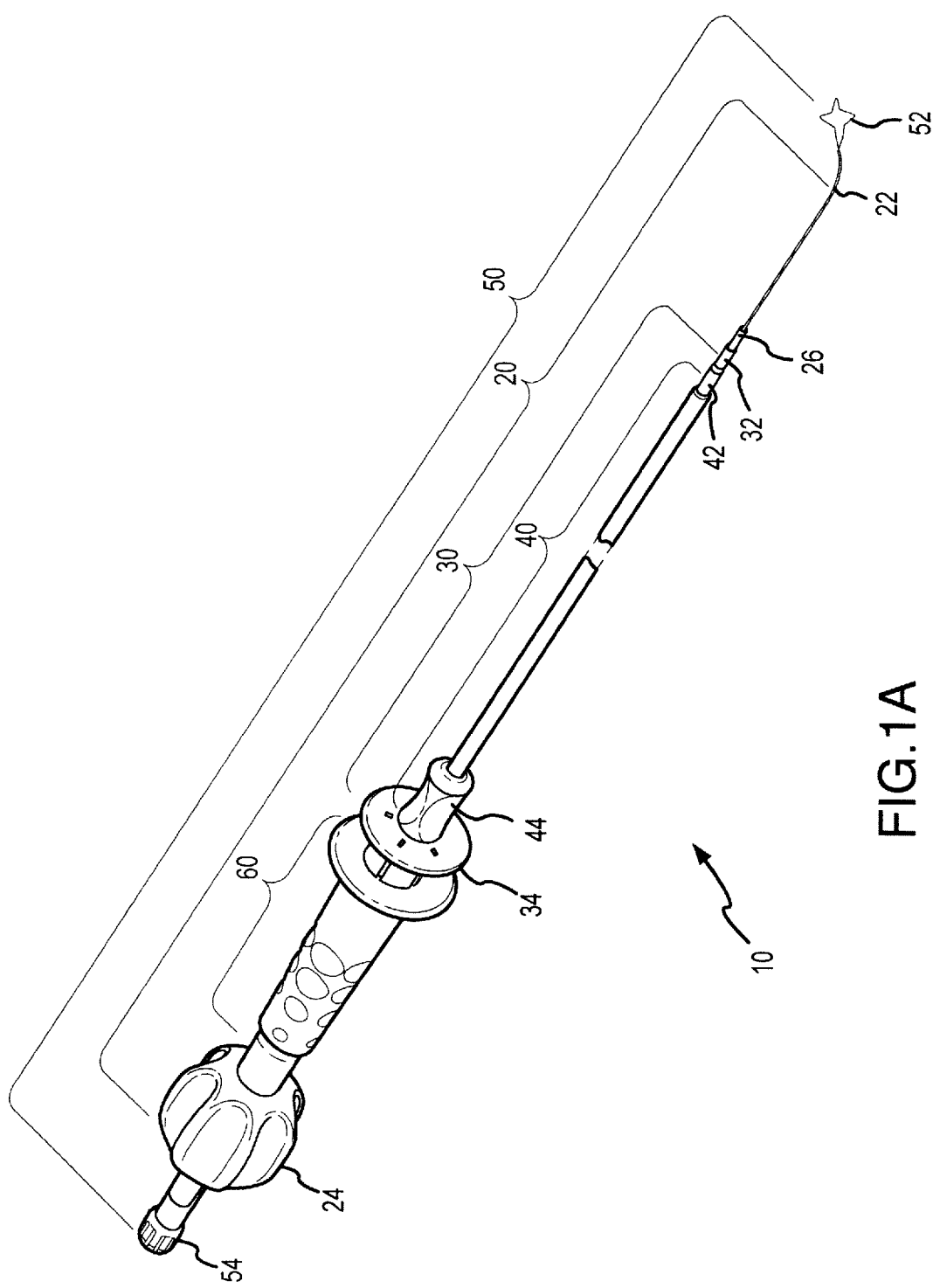
FIGS. 1A and 1B are isometric views of alternate embodiments of an apparatus comprising the present invention.

The suturing apparatus (10) shown in FIG. 1A comprises an elongated needle assembly (20) having a hollow piercing tip (22) at one end and a rotatable and advanceable/retractable handle (24) at a proximal end. Needle assembly (20) further includes a bobbin (26) about which a length of suturing material with a pre-tied knot may be disposed (not shown in FIG. 1A). In this regard, suturing apparatus (10) also includes a knot positioning assembly (30) having a pusher end (32) positionable adjacent to the bobbin (26) of the needle assembly (20), and further having a selectively advanceable/retractable handle (34) at a proximal end.

Suturing apparatus (10) also includes a suture cutter assembly (40) comprising a distal end (42) with a suture cutting surface positionable adjacent to the pusher end (32) of knot positioning assembly (30) and bobbin (26) of needle assembly (20). The suture cutter assembly (40) further includes an advanceable/retractable handle (44) at a proximal end. Suture apparatus (10) also includes a suture grasping assembly (50) having a hoop member (52) disposed at a distal end for selective retraction within/advancement out of the hollow piercing tip (22) of needle assembly (20), and further having a selectively advanceable/retractable and rotatable handle (54) provided at a proximal end. Finally, suturing apparatus (10) includes a proximal primary handle portion (60) for use in manipulating the suturing apparatus (10).

As will be appreciated, from an inside-out perspective, grasping assembly (50), needle assembly (20), knot positioning assembly (30) and suture cutter assembly (40) are disposed in concentric coaxial relation for separate and selective advancement/retraction and/or rotation relative to one another. Further, grasping assembly (50) and needle assembly (20) may be disposed with a predetermined frictional interface to permit co-rotation if desired. Similarly, proximal handle (24) of needle assembly (20) and primary handle (60) may be disposed with a predetermined frictional interface to facilitate co-rotation if desired. In this regard, reference is now made to FIGS. 2A and 3A which illustrate distal and proximal cross-sections of the suturing apparatus (10) of FIG. 1A, respectively.

Figure 2A:
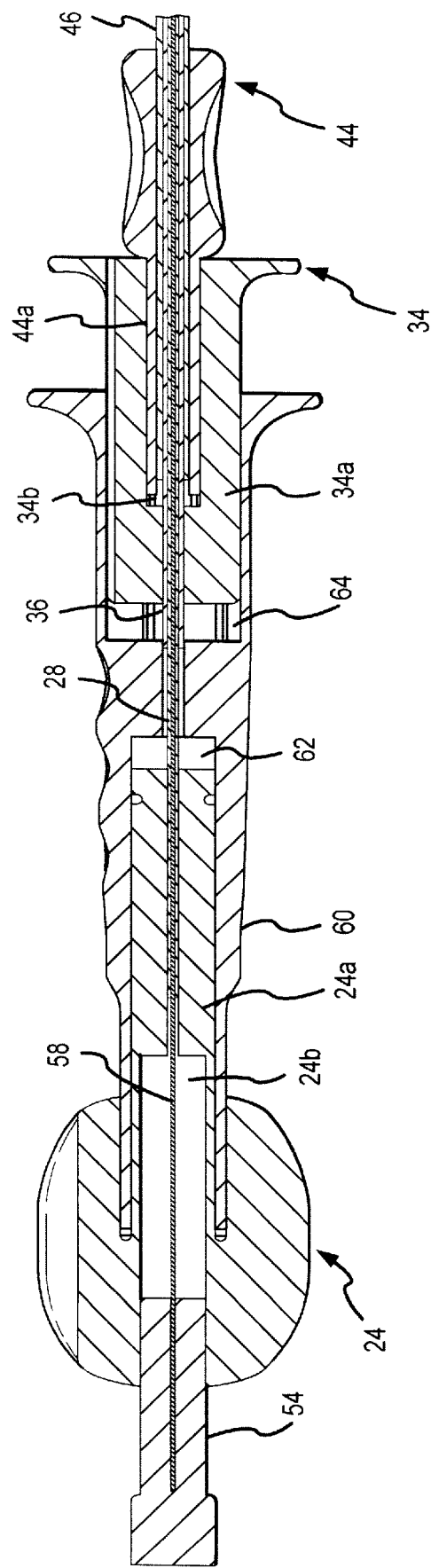
FIGS. 2A and 2B are cross-sectional views of proximal end portions of the embodiments of FIG. 1A and 1B, respectively.
Figure 3A:
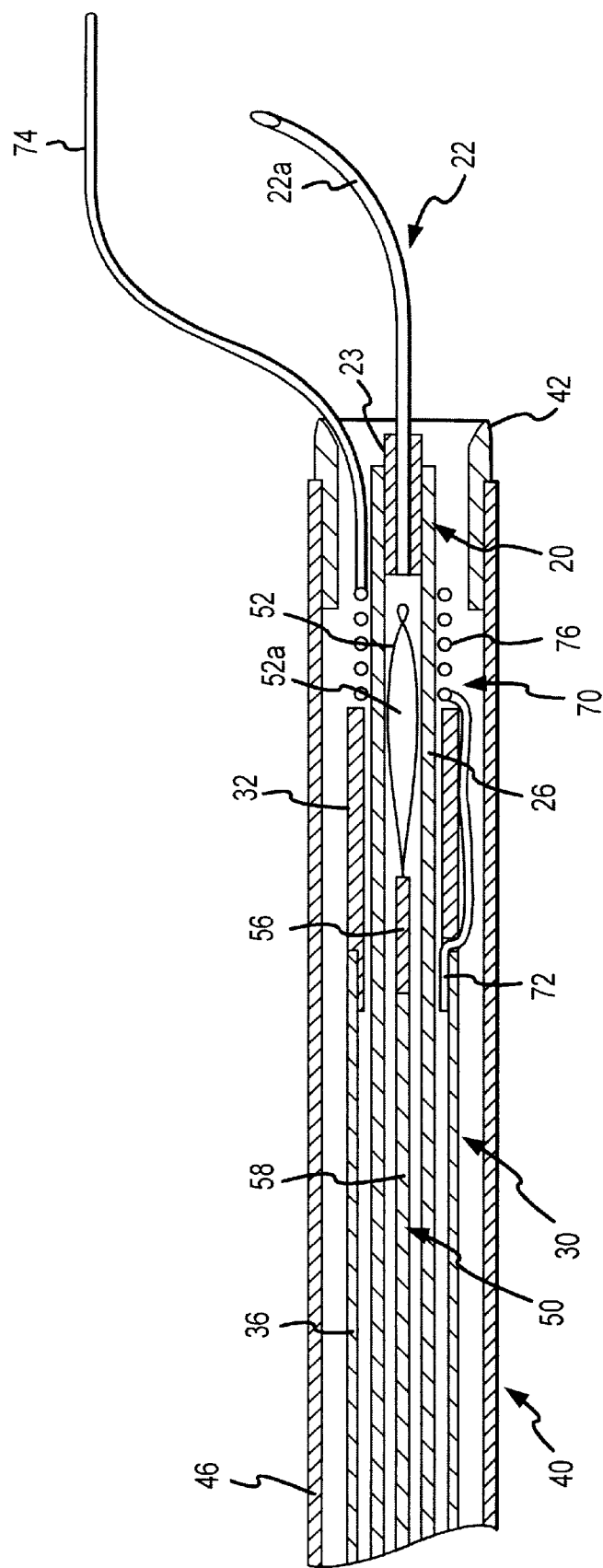
FIGS. 3A and 3B are cross-sectional views of distal end portions of the embodiments of FIGS. 1A and 1B, respectively.

With particular respect to grasping assembly (50), FIG. 3A illustrates hoop member (52) in a retracted, non-deployed position within needle assembly (20). In this regard, it should be noted that hoop member (52) may be constructed of a wire-like material shaped to define a hoop having an opening (52a) therethrough. As will be subsequently described, when hoop member (52) is advanced through the distal tip of the piercing end (22) of the needle assembly (20) the hoop member (52) will automatically spring open into a predefined shape (e.g., a diamond configuration) for selective positioning about and grasping of a suture material in the suturing process. Note that the distal end of hoop member (52) preferably defines an internal angle θ of at least about 15° when deployed. The ends of the wire-like material utilized to define hoop member (52) may be interconnected to neck portion (56) via two receiving grooves formed therein, and neck portion (56) may in turn be fixedly interconnected to a rod member (58) that extends substantially the length of the suturing apparatus (10) to adjoin the proximal handle (54) as shown in FIG. 2A. In the latter regard, it can be seen in FIG. 2A, that handle (54) is disposed for rotatable and slideable engagement through the handle (24) of the needle assembly (20). For such purposes, an aperture (24b) is formed through the handle (24).

Figure 4:
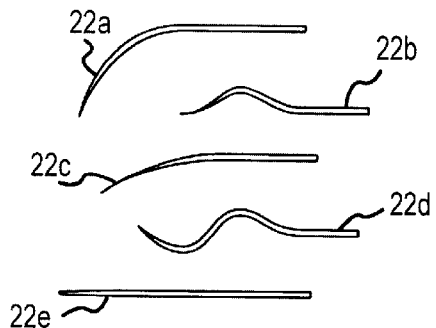
FIG. 4 illustrates five alternate piercing tips employable with the disclosed embodiments.

With respect to needle assembly (20), FIG. 3A illustrates that the piercing tip (22) may be defined by a separate end section (22a) and an intermediate member (23) secured within an open-end of bobbin portion (26). In this regard, it should noted that a variety of different end section shapes may be utilized. In particular, FIG. 4 shows a number of different piercing tip end sections (22a–22e). Each of the end sections (22a–22e) may provide particular functional advantages in different applications. For example, end section (22a) may be used for suturing on flat co-planar surfaces; end section (22b) may be used for suturing ridges or undulating co-planar surfaces; end section (22c) may be used for shallow stitching; end section (22d) is helical for suturing stubborn tissue that is more muscular; and end section (22e) may be used for general purpose suturing.

Returning now to FIGS. 2A and 3A, it should be noted that bobbin (26) of the needle assembly (20) may be interconnected to a driver tube (28) that extends the substantial length of suture apparatus (10) for interconnection with proximal handle (24). In this regard, and as best shown in FIG. 2, the rod member (58) of grasping assembly (50) is slidably received within driver tube (28) of the needle assembly (20). In turn, the proximal end of driver tube (28) is interconnected to an internal shaft portion (24a) of the proximal handle (24). Shaft portion (24a) is sized for slideable receipt within an opening (62) of the primary handle (60) of suturing apparatus (10).

Referring again now to FIG. 3A, a length of suture material (70) is shown wound about the bobbin (26) of the needle assembly (20). A first end (72) of the suture material (70) is interconnected to the pusher end (32) of knot positioning assembly (30) while a second free end (74) of the suture material (70) is shown in a position extending away from pusher end.(32) of the knot positioning assembly (30). The wound portion (76) of suture material (70) includes a pre-tied knot (e.g., a Roeder knot). It should be noted that in connection with the use of suture apparatus (10) the second end (74) of the suture material (70) may be grasped and pulled through the hollow piercing tip (22) of the needle assembly (20) by hoop member (52) of the grasping assembly (50). Further, during use of suture apparatus (10) the pre-tied knot portion (74) may be selectively positioned by use of the knot positioning assembly (30). That is, handle (34) of knot positioning assemble (30) may be selectively advanced and/or handle (24) of needle positioning assembly

(20) may be selectively retracted so that the pre-tied knot of suture material (70) is "dropped" beyond the distal end of needle assembly (20).

With further respect to knot positioning assembly (30), FIG. 3A illustrates that the pusher end (32) may be defined by a separate piece that fits within the end of an elongated tube member (36). In turn, the elongated tube member (36) extends the substantial length of suturing apparatus (10) for interconnection with the proximal handle (34). In this regard, and as best shown in FIG. 2A, the driver tube (28) of needle assembly (20) may be slideably received within the tube member (36) of the knot position assembly (30). In turn, the proximal end of tube member (36) may be interconnected to an internal shaft portion (34a) of the proximal handle (34). Shaft portion (34a) is sized for slideable receipt within a cylindrical opening (64) of primary handle (60) of suturing apparatus (10).

As to suture cutter assembly (40), FIG. 3A illustrates that a separate member may define the distal cutting end (42). In turn, the distal end member (42) may be securely received within the open end of an elongated tube member (46) that extends the substantial length of suturing apparatus (10). As best shown in FIG. 2A, the tube member (36) of knot positioning assembly (30) may be slideably received within the tube member (46) of the suture cutter assembly (40). The proximal end of tube member (46) may be interconnected to an internal shaft portion (44a) of the proximal handle (44). Shaft portion (44a) is sized for slideable receipt within a cylindrical opening (34b) of the proximal handle (34) of the knot positioning assembly (30).

Figure 1B:
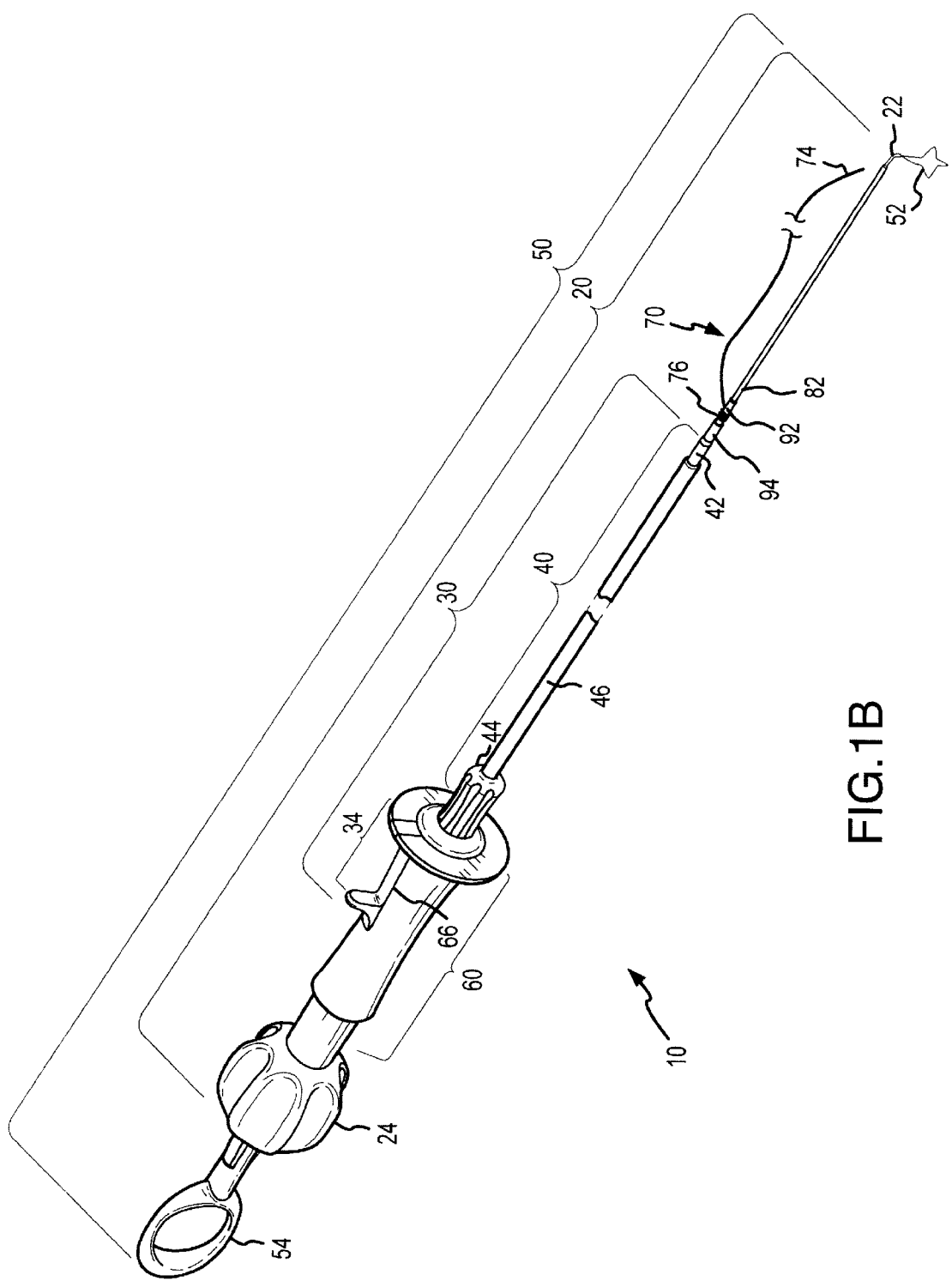
Figure 2B:
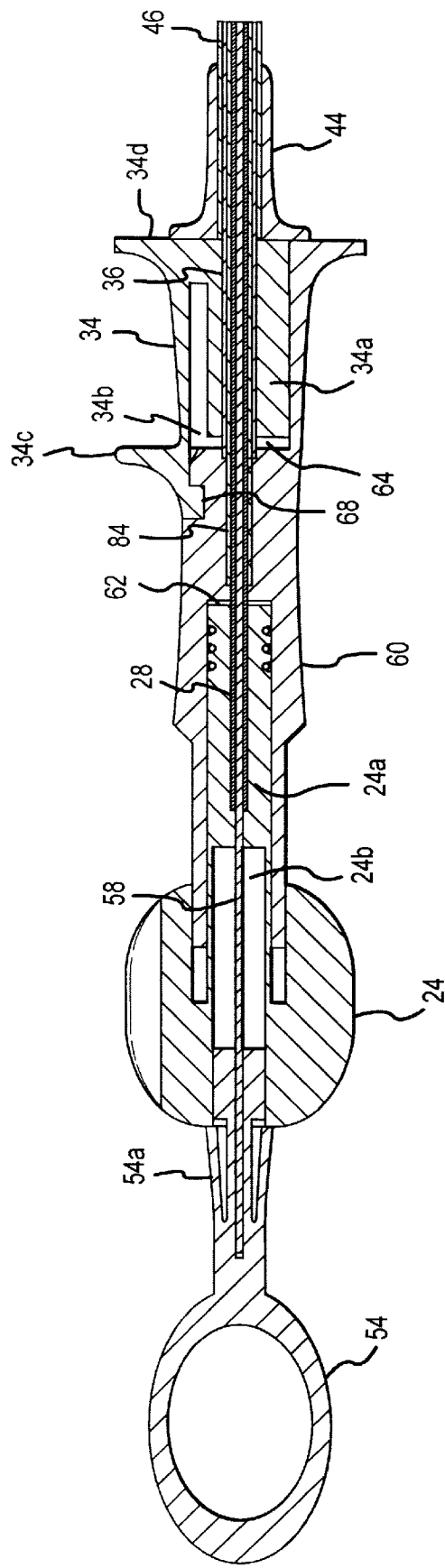
Figure 3B:
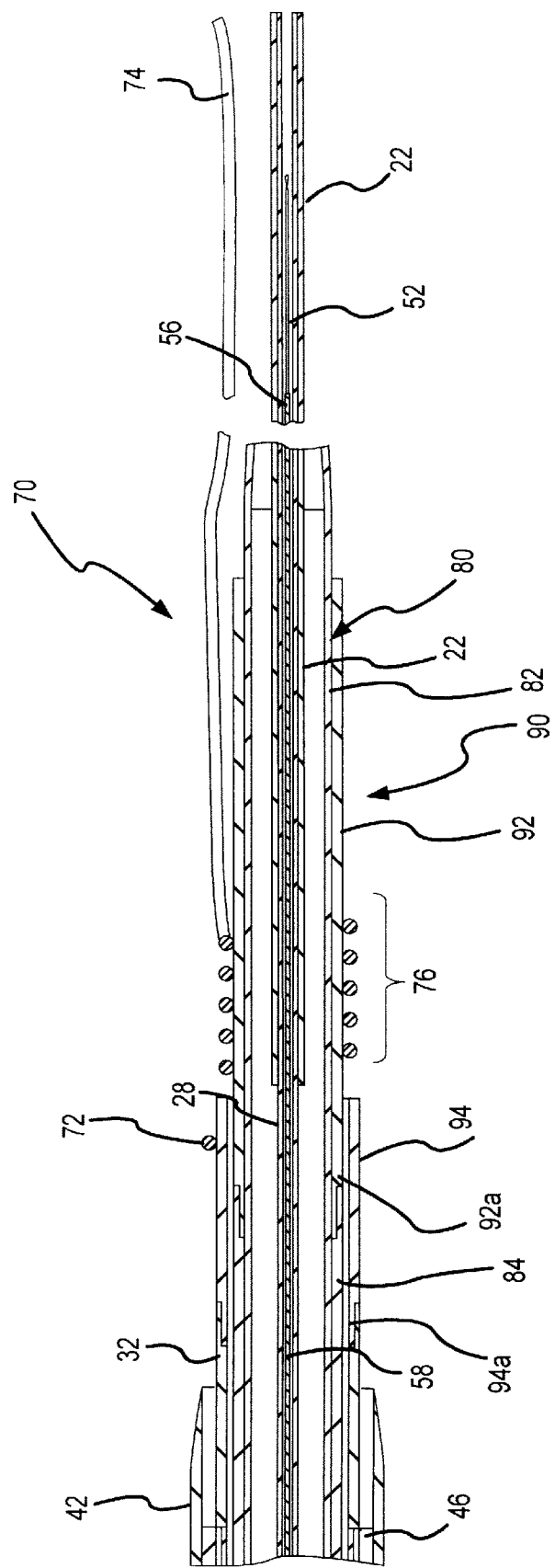

Referring now to FIGS. 1B, 2B and 3B, an alternate embodiment of suturing apparatus (10) is illustrated. As may be appreciated, the embodiment shown in FIGS. 1B, 2B and 3B is quite similar to embodiment of FIGS. 1A, 2A and 3A. As such, common reference numerals are utilized and the description provided above with respect to the commonly employed reference numerals is applicable. However, a number of additional features in the embodiment of FIGS. 1B, 2B and 3B should be noted.

In particular, and as best shown by FIG. 3B, the illustrated suturing apparatus (10)further comprises a guide assembly (80) and a suture carrier assembly (90). The guide assembly (80) functions as a guide for the needle assembly (20) and also supports the suture carrier assembly (90). Guide assembly (80) comprises an inner member (82) and an outer member (84) interconnected with the inner member (82). The outer member (84) extends from the distal region of suturing apparatus (10) to the proximal end thereof where it is interconnected with the primary handle (60), as shown in FIG. 2B.

The suture carrier assembly (90) carries suture material (70) and comprises a spool member (92) and an interconnect member (94). The carrier assembly (90) is sized for slidable, concentric positioning over the end of the inner member (82) of the guide assembly (80). The interconnect member (94) is provided with a proximal end (94a) that is adapted for snap fit interconnection with the pusher end (32) of the knot positioning assembly (30). Relatedly, spool member (92) is provided a proximal end 92a that is adapted for snap fit interconnection with a distal end of the outer member (84) of the guide assembly (80). As shown in FIG. 3B, a proximal end (72) of suture material (70) is anchored to interconnected member 94 and the wound portion (76) comprising a pre-tied knot is initially located about the spool member (92). As such, upon advancement of pusher end (32) the interconnect member (94) will advance relative to spool member (92) to engage the wound portion (76) and thereby "drop" the pre-tied knot beyond the end of spool member (92) as desired.

By virtue of the inclusion of guide assembly (80) and carrier assembly (90), it may be appreciated that multiple suturing procedures and re-use of suturing apparatus (10) is facilitated. That is, after a given tissue stitching/knot placement procedure, the suturing apparatus (10) may be removed from a patient's body and a new carrier assembly (90) may be readily installed for subsequent use. Certainly, such an arrangement accommodates the provision of suture carrier assembly (90) as a disposable item, wherein spool member (92) and interconnect member (94) are of plastic construction and are assembled packaged with suture material (70) for separate distribution and storage.

Referring now to FIGS. 1B and 2B, additional distinctive features of the embodiment will be noted. In particular, proximal handle (54) of the grasping assembly (50) is provided with one or more finger members (54a) that are disposed to abut proximal face of the proximal handle (24) of the needle assembly (20) and thereby restrict undesired distal advancement of the hoop member (52) of the grasping assembly (50). When such advancement is desired, the finger members (54a) may be squeezed towards the central axis of the proximal handle (54), thereby allowing the finger members (54) to be slidably received into the aperture (24b) of the proximal handle (24).

As further illustrated by FIGS. 1B and 2B, the knot positioning assembly (30) is also provided with a modified proximal handle (34). More particularly, proximal handle (34) includes a cantilevered slide tab (34c) that is disposed for selective, slidable advancements/retraction within an aperture (66) formed in the primary handle (60). Further, a proximal end of slide tab (34c) is enlarged for selective locking engagement interlocking receipt within a recess (68) formed in primary handle (60). Such locking engagement restricts unintended advancement of the knot positioning assembly (30) during use of the suturing apparatus (10). When advancement is desired, a user may simply push the primary flange (34d) provided on handle (34) and/or slide tab (34c) distally, wherein opposing ramped portions (not shown) of the enlarged proximal end of the slide tab (34c) and recess (68) urge cantilevered slide tab (34c) to slightly pivot outward and advance distally.

As noted, the suturing apparatus (10) of both embodiments is particularly adapted for endoscopic applications. In this regard, it may be appreciated that portions of the grasping assembly (50), needle assembly (20), knot positioning assembly (30) and suture cutter assembly (40) may be of a flexible construction to allow for passage through an endoscope designed for passage through oral, anal, and other endoscopic access locations/canals.

Further, for typical endoscopic applications, the length of driver tube (28), tube members (36) and (46), as well as the combined length of members (56) and (58), should preferably be at least about 70" (and at least about 5" for laparoscopic applications), and the outer diameter of tube member 46 of the suture cutter assembly (40) should preferably not exceed about 0.562". Correspondingly, the outer diameters of tube member (36), driver tube (28) and rod member (58) should be established in a decreasing, stepwise fashion. In this regard, it has been determined that the outer diameter of rod member (58) of the grasping assembly (50) should preferably be between about 0.015" and 0.048", while the outer diameter for the tube member (28) of the needle assembly (20) should preferably be between about 0.020" and 0.062". Additionally, in order to provide the desired control over hoop member (52) and piercing tip (22), it is preferable that the grasping assembly (50) and needle assembly (20) each have a torsional strength of at least about 0.02 in. lb. and a buckle strength of at least about 0.2 psi along their respective lengths.

In order to accommodate such sizing and strength characteristics it has been found that rod member (58), hoop member (52) and neck (56) of the grasping assembly (50), driver tube (28) and piercing tip (22) of the needle assembly (20), pusher tube (32) and tube member (46) may comprise nickel, titanium and nickel titanium alloys. It is believed that other materials which may be employed for such componentry include: spring steel, stainless steel, reinforced plastic sheathing (i.e., catheter tube), braided wire tubing.

Figures 6A, 6B:
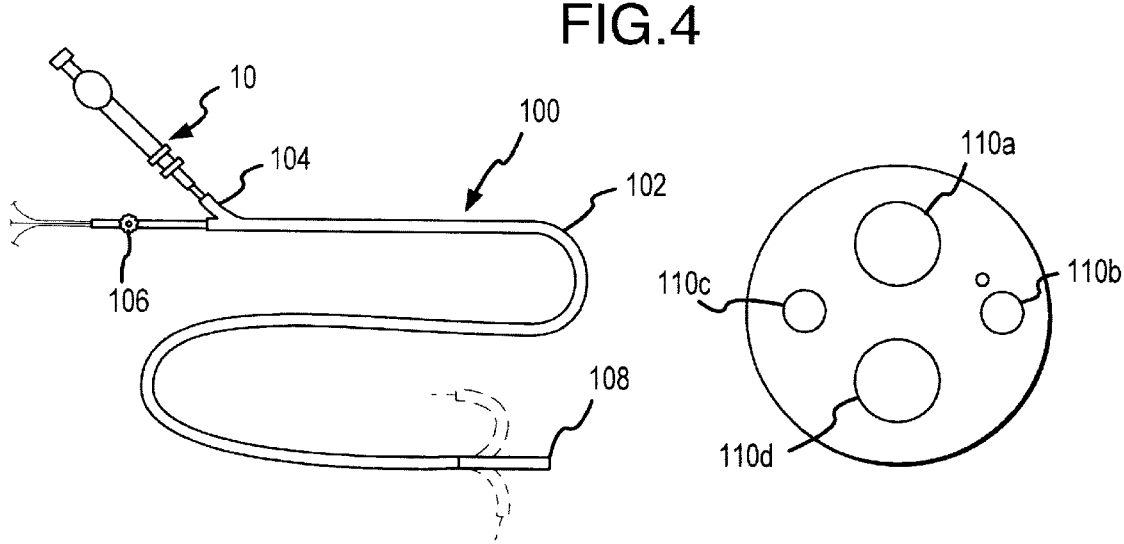
FIG. 6A illustrates an endoscopic system application use of the embodiment of FIG. 1A.
FIG. 6B is an end view of an endoscope employable with the system of FIG. 6A.
Figure 6C:
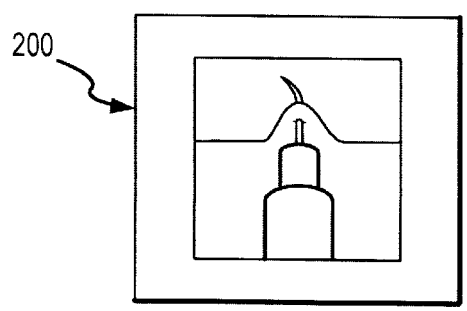
FIG. 6C illustrates a display device employable in the system of FIG. 6A.
Figure 5A:
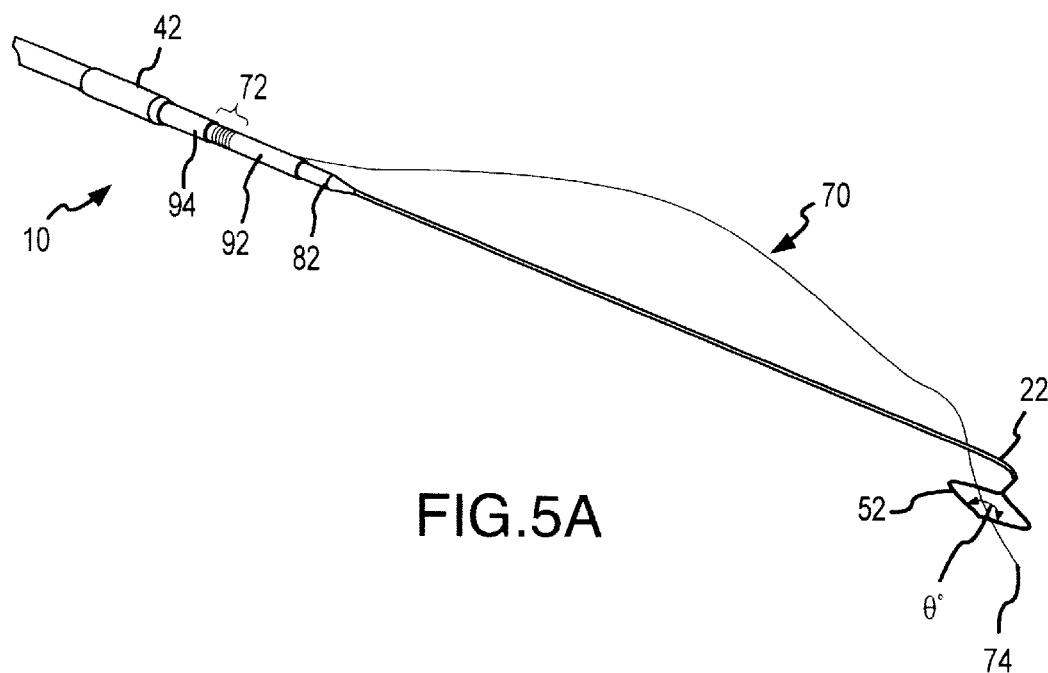
FIGS. 5A and 5B are isometric views of the grasping assembly of the embodiment of FIGS. 1B, 2B and 3B, in advanced and retracted positions, respectively.
Figure 5B:
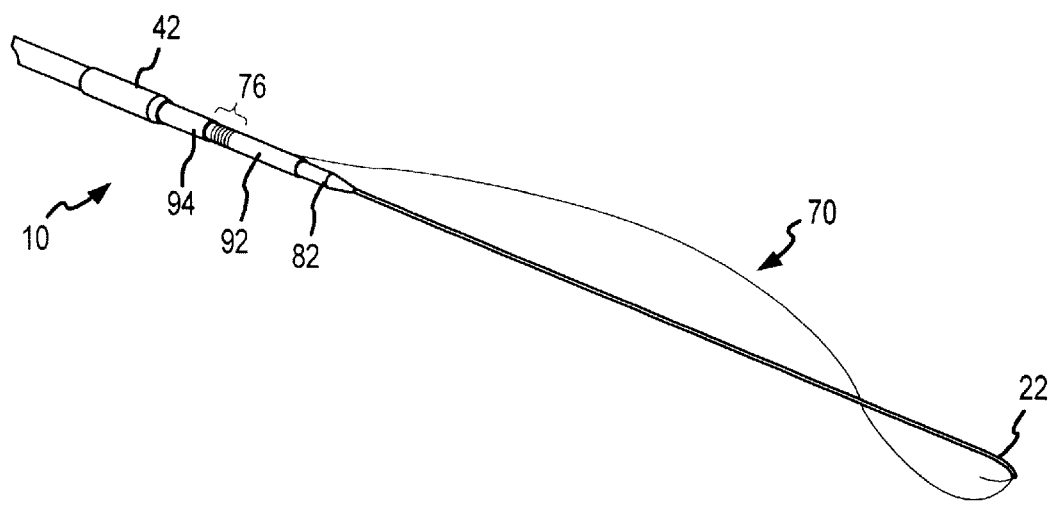

Referring now to FIGS. 6A–6C, an endoscopic device (100) is illustrated with suturing apparatus (10) positioned within a tubular member (102) via insertion through a side port (104). As will be appreciated, the endoscopic device (100) may comprise a control device (106) for externally maneuvering the distal end (108) of the endoscopic device (100) so as to facilitate selective access a tissue region of interest within a patient body.

In this regard, endoscopic device (100) may comprise a number of channels passing therethrough with separate ports at the distal end (108). By way of example, and referring now to FIG. 6B, separate ports (110a), (110b), (110c) and (110d) may be provided for the positioning of an imaging device, light sources, and an irrigation device therewithin, respectively. Port (110d) may be provided for the selective passage of an instrument, such as suturing apparatus (10) therethrough. When suturing apparatus (10) is positioned through endoscopic device (100) for access to a tissue site, the suturing apparatus (10) can be advanced/retracted within a field of view of an imaging device located the distal end (108). In this regard, FIG. 6C illustrates how suturing apparatus (10) may be viewed when utilized with an endoscopic apparatus (100) having an imaging device interconnected with a real-time user display (200). As illustrated, the piercing tip (22) of needle assembly (20), projects into a field of view defined by the imaging device positioned at the distal end (108) so that suturing maneuvers may be readily observed/controlled.

Referring now to FIGS. 7A–7T, an exemplary two-stitch suturing procedure in an endoscopic application will be described. As will be appreciated, prior to such procedure an endoscopic device (100) will have been inserted into a patient body with the distal end (108) positioned adjacent to a tissue region of interest. Further, endoscopic device (10) may have been employed to conduct a medical procedure with respect to the tissue site, e.g., a surgical procedure in which surgical instrumentation is manipulated through port (110d) of the endoscopic device (100) to effect a surgical incision (300) and then removed.

As illustrated in FIG. 7A, it can be seen that suturing apparatus (10) has been advanced through endoscopic device (100) so that the piercing tip (22) of the needle assembly (20) projects from port (110d) at the distal end (108) of the endoscopic device (100) adjacent to surgical incision (300). In the illustrated embodiment, the free end (74) of the suture material (70) has been grasped within the hoop member (52) of the grasping assembly (50) and pulled into the end of hollow piercing tip (22). Such grasping may be conveniently completed prior to insertion of the suturing apparatus (10) into the endoscopic device (100). Upon advancement of the piercing tip (22) to the desired position relative to the incision (300), e.g., via manipulation of an endoscopic control, needle assembly handle (24) may be rotated so as to rotate piercing tip (22) into contact with tissue at the incision (300).

Thereafter, and as shown in FIG. 7B, needle assembly handle (24) may be utilized to advance the piercing tip (22) into the tissue a desired distance. Then, needle assembly handle (24) may be rotated to effect a rotation of the piercing tip (22) back out of the tissue to create a partial lifting action at incision site (300), as shown in FIG. 7C. As illustrated, the controlled advancement/rotation of piercing tip (22) will cause suture material (70) to be pulled through the tissue on a first side (302) of the surgical incision (300). At this point, handle (54) may then be utilized to advance hoop member (52) out of the hollow end of piercing tip (22) and then rotated so as to disengage or release the free end (74) of suture material (70) therefrom as shown in FIG. 7D. Thereafter, handle (54) may be manipulated so that hoop member (52) is retracted back into the piercing tip (22) and handle (24) may be utilized to withdraw piercing tip (22) back out of tissue as on the first side (302) of incision (300) shown in FIG. 7E.

Then, handle (54) of the grasping assembly (50) may be advanced to again deploy hoop member (52) out of the end of piercing tip (22) as shown in FIG. 7F. As further shown in FIG. 7F, hoop member (52) may be rotated and advanced so as to selectively position the free end (74) of suture material (70) therethrough. Upon such positioning, and as illustrated in FIG. 7G, hoop member (52) may again be retracted into the end of hollow piercing tip (22) with the free end (74) of suture material (70) grasped thereby.

As shown in FIG. 7H, suturing apparatus (10) may then be positioned and piercing tip (22) may be rotated via needle assembly handle (54) into contact with the tissue on a second side (304) of incision (300). Piercing tip (22) may then be advanced a desired distance through the tissue as shown in FIG. 7I, and rotated to exit the tissue on second side (304) through the incision (300) as illustrated in FIG. 7J. As shown in FIG. 7K, hoop member (52) may be advanced again out of piercing tip (22) to release the end portion (74) of suture material (70). Hoop member (52) may then be retracted into the end of piercing tip (22), with the end portion (74) of suture material left protruding from the incision (300) as shown in FIG. 7L. Once again, piercing tip (22) may then be withdrawn from the tissue as illustrated in FIG. 7M, followed by the advancement of hoop member (52) out of the end of piercing tip (22). Hoop member (52) is then rotated for positioning about the protruding end (74) the suture material as shown in FIG. 7N. Upon such positioning, hoop member (52) may then be retracted into the end of distal tip (22) so as to grasp the end portion (74) of suture material (70) as shown in FIG. 7O.

Thereafter, piercing tip (22) and/or suturing apparatus (10) may be retracted or withdrawn so as to tighten the stitching at the incision site (300), as shown in FIG. 7P. While maintaining tension upon the suture material (70), knot positioning assembly handle (34) may be advanced relative to piercing tip (22) so as to push the pre-tied knot (76) about and off the end of piercing tip (22), as shown in FIG. 7Q. As illustrated in FIG. 7R, the distal end (32) of knot positioning assembly (30) may then be further advanced to position the pre-tied knot portion (76) adjacent to the incision site (300). Then, as illustrated in FIG. 7S, the distal end (32) of the knot positioning assembly (34) may again be retracted and suturing apparatus (10) and/or needle assembly (20) may be manipulated to further tighten the knot portion (76) at the incision (300). Finally, needle assembly (24) may be rotated and/or suturing apparatus (10) may be otherwise manipulated to cause suturing material (70) to contact a surface of distal end 42 of the suture cutter assembly 40 and thereby sever the suture material (70), as shown in FIG. 7T.

Thereafter, suturing apparatus (10) may be withdrawn from the distal end (108) endoscopic device (100) to complete the suturing procedure. Alternatively, another suture carrier assembly (90) may be installed after which the suturing apparatus (10) may be reinserted into the endoscopic device (100) for the completion of an additional suture procedure. Such procedure may be repeated as many times as may be desired by medical personnel to effect the desired suturing result.

The embodiment and method described above is for exemplary purposes only and is not intended to limit the scope of the present invention. Numerous adaptations, modifications and extensions of the described apparatus and methods will be apparent to those skilled in the art and are intended to be within the scope of the present invention as defined by the claims which follow.

What is claimed is:

1. A suturing apparatus, comprising:
   a needle having a distal end portion;
   suture material having a pre-tied knot initially concentrically disposed about the distal end portion of the needle; and
   a first member located adjacent to said distal end portion of the needle, wherein said first member and the needle are interconnected to permit selective relative movement therebetween, and wherein upon said selective relative movement the first member is engagable with said suture material to position said pre-tied knot beyond a distal end of the needle.

2. An apparatus as recited in claim 1, wherein said distal end portion of the needle comprises:
   an arcuate piercing tip.

3. An apparatus as recited in claim 2, further comprising:
   a handle interconnected to a proximal end portion of the needle, wherein rotation of said handle effects substantially co-rotational movement of a free end of said arcuate piercing tip through a corresponding arc.

4. An apparatus as claimed in claim 3, wherein said needle has a torsional strength of at least about 0.02 in. lb. from said proximal end portion to said distal end portion.

5. An apparatus as recited in claim 3, wherein said needle comprises a resilient material to permit flexural curvature along a length thereof.

6. An apparatus as recited in claim 5, wherein said needle is of an elongated construction from said proximal end portion to said distal end portion.

7. An apparatus as recited in claim 1, wherein one end of said suture material is anchored to said first member, and wherein said needle and first member are interconnected for selective, co-rotational movement.

8. An apparatus as recited in claim 1, further comprising:
   a second member having a distal surface adapted for cutting said suture material, wherein said second member and at least one of said first member and said needle are disposed to permit selective relative movement therebetween.

9. An apparatus as recited in claim 1, wherein said needle comprises a material selected from a group consisting of: nickel titanium alloy, nickel, titanium, stainless steel and surgical steel.

10. A suturing apparatus, comprising:
    a suture needle having a distal end;
    suture material having one end anchored adjacent to said distal end of said suture needle; and
    a grasping member, wherein said suture needle and said grasping member are interconnected to permit selective relative movement therebetween, and wherein upon said selective relative movement a distal end of said grasping member is positionable from within the suture needle to beyond the distal end of said suture needle for grasping said end portion of said suture material.

11. An apparatus as recited in claim 10, wherein said distal end of the grasping member telescopes through an opening of the suture needle upon said selective relative movement.

12. An apparatus as recited in claim 10, wherein said distal end of the grasping member comprises:
    a spring-loaded portion, wherein said spring-loaded portion collapses to a non-deployed state upon selective positioning within said distal end of said suture needle and automatically springs open to a deployed state upon positioning beyond said distal end of the suture needle.

13. An apparatus as recited in claim 12, wherein said spring-loaded portion is of a hoop-like configuration for selective positioning about an end portion of said suture material in said deployed state and for capturing said end portion therethrough in said non-deployed state.

14. An apparatus as recited in claim 13, wherein said spring-loaded portion defines an internal angle at its distal extreme of at least about 15° when the spring-loaded portion is in a said deployed state.

15. An apparatus as recited in claim 11, further comprising:
    a handle interconnected to a proximal end portion of the grasping member, wherein rotation of said handle effects substantially co-rotational movement of said distal end of the grasping member.

16. An apparatus as recited in claim 15, wherein said grasping member has a torsional strength of at least about 0.02 in. lb. from said proximal end portion to said distal end of the grasping member.

17. An apparatus as recited in claim 10, wherein said suture needle and said grasping member each comprising material from a group consisting of: nickel titanium alloy, nickel, titanium, stainless steel and surgical steel.

18. An apparatus as recited in claim 10, further comprising:
    a first member located adjacent to said distal end of the suture needle, wherein said first member, said suture needle and said grasping member are disposed to permit selective relative movement therebetween, and wherein said first member is positionable to engage said suture material to position a pre-tied knot thereof beyond said distal end of the suture needle.

19. An apparatus as recited in claim 18, further comprising:
    a handle slideably interconnected with a proximal end portion of said grasping member and fixedly interconnected with a proximal end portion of said suture needle.

20. An apparatus as recited in claim 18, further comprising:
    a second member having a distal surface adapted for cutting said suture material, wherein said second member and at least one of said first member and said suture needle are disposed to permit selective relative movement between.

21. A method for suturing comprising: retaining an end portion of a suture material at a distal end of a suture needle;
advancing a limited portion of said suture needle along a path through a patient tissue site, wherein said suture material is pulled through the patient tissue site by said suture needle;
releasing said end portion of the suture material from retention by said distal end of said suture needle;
withdrawing said limited portion of said suture needle back along said path through said patient tissue site, wherein said end portion of the suture material is left protruding from the patient tissue site;
grasping said protruding end portion of said suture material; and
positioning a pre-tied knot portion of said suture material about said end portion thereof.

22. A method as recited in claim 21, wherein said retaining step includes:
grasping said end portion of said suture material; and,
pulling said grasped end portion of said suture material into a hollow piercing tip at said distal end of the suture needle.

23. A method as recited in claim 22, wherein said releasing step includes:
advancing said grasped end portion out of the hollow piercing tip at the distal end of said suture needle.

24. A method as recited in claim 21, wherein said positioning step includes:
advancing said pre-tied knot portion of said suture material relative to said end portion thereof to tighten said pre-tied knot portion adjacent to said tissue site.

25. A method as recited in claim 22, wherein said positioning step further includes:
pulling said grasped end portion of said suture material into a hollow piercing tip at the distal end of said suture needle.

26. A method as recited in claim 23, wherein said pre-tied knot portion is initially positioned about said suture needle, and wherein said positioning step further includes:
pushing said pre-tied knot portion off of said suture needle.

27. A method as recited in claim 21, wherein said grasping step includes:
positioning a spring-loaded, hoop-shaped member about said protruding end portion of the suture material; and
retracting said spring-loaded, hoop-shaped member into a hollow piercing tip at the distal end of the suture needle.

28. A method as recited in claim 21, further comprising:
inserting a surgical instrument through a tubular member having a distal end adjacent to said patient tissue site; and
externally manipulating said suturing instrument to complete each of said retaining, advancing, releasing, withdrawing, grasping and positioning steps.

29. A method as recited in claim 28, further comprising:
imaging each of said retaining, advancing, releasing, withdrawing, grasping and positioning steps at said distal end of said tubular member.

30. A suturing system, comprising:
a tube member adapted for insertion into a patient body;
an imaging apparatus positioned through said tube member for acquiring images within an image view range at a distal end of said tube member; and
a suturing device positioned through said tube member for suturing adjacent to said distal end of said tube member, said suturing device including a suture needle having a proximal end portion extending from a proximal end of said tube member, said proximal end portion of the suture needle being manipulatable to selectively advance and retract a distal end of the suture needle within said image view range of said imaging device.

31. A system as recited in claim 30, wherein said suturing device further comprises:
a suture material having a pre-tied knot disposed about a distal end portion of said suture needle; and
a first outer member, wherein said suture needle and first outer member are disposed to permit selective relative movement therebetween, and wherein upon said selective relative movement said first outer member disposes said at least partially pre-tied knot beyond said distal end portion of said suture needle for selective tightening within said image view range of said imaging device.

32. A system as recited in claim 31, further comprising:
a display device interconnected to said imaging apparatus for displaying said acquired images to a user on a real-time basis.

33. A system as recited in claim 31, wherein said suture needle comprises:
an arcuate piercing tip.

34. A system as recited in claim 33, wherein rotation of said proximal end portion of said suture needle effects substantially co-rotational movement of a free end of said arcuate piercing tip to a corresponding arc within said image view range of said imaging device.

35. A suturing apparatus as recited in claim 10, wherein said suture needle comprises:
an arcuate piercing tip.

36. An apparatus as recited in claim 30, wherein said suturing device further comprises:
suture material having a pre-tied knot; and,
a grasping member for selectively grasping an end portion of said suture material within said image view range.

37. An apparatus as recited in claim 36, wherein said pre-tied knot is initially concentrically disposed about said grasping member.

38. An apparatus as recited in claim 37, wherein said pre-tied knot is supportably disposed on said distal end portion of said suture needle.

39. An apparatus as recited in claim 38, wherein said suture needle and said grasping member are disposed to permit selective relative movement therebetween, and wherein upon said selective relative movement a distal end of said grasping member is positionable beyond the distal end of said suture needle for grasping said end portion of said suture material.

40. A suturing apparatus, comprising:
suture material having an end portion and a pre-tied knot;
a needle, wherein said pre-tied knot is disposed about the needle; and,
a grasping member, disposed for selective movement relative to said pre-tied knot, for selectively grasping and retaining said end portion of said suture material through said pre-tied knot.

41. An apparatus as recited in claim 40, wherein said pre-tied knot is concentrically disposed about a distal end portion of the needle.

42. An apparatus as recited in claim 41, wherein said pre-tied knot is supportably disposed on said distal end portion of said needle.

43. An apparatus as recited in claim 41, wherein said pre-tied knot is concentrically disposed about said grasping member.

44. An apparatus as recited in claim 43, wherein said needle and said grasping member are disposed to permit selective relative movement therebetween, and wherein upon said selective relative movement a distal end of said grasping member is positionable beyond the distal end of said needle for grasping said end portion of said suture material.

45. An apparatus as recited in claim 44, wherein said distal end of the grasping member is selectively positionable from within said distal end of said suture member to telescope therebeyond upon said selective relative movement.

46. An apparatus as recited in claim 45, wherein said distal end of the grasping member comprises:
   a spring-loaded portion, wherein said spring-loaded portion collapses to a non-deployed state upon positioning within said distal end of said needle and automatically springs open to a deployed state upon positioning beyond said distal end of the needle.

47. An apparatus as recited in claim 46, wherein said spring-loaded portion is of a hoop-like configuration for selective positioning about said end portion of said suture material in said deployed state and for capturing said end portion therethrough in said non-deployed state.

48. An apparatus as recited in claim 47, wherein said spring-loaded portion defines an internal angle at its distal extreme of at least about 15° when the spring-loaded portion is in said deployed state.

49. An apparatus as recited in claim 45, wherein said grasping member further comprises:
   a proximal end portion, wherein rotation of said proximal end portion effects substantially co-rotational movement of said distal end of the grasping member in said deployed state.

50. An apparatus as recited in claim 49, wherein said grasping member has a torsional strength of at least about 0.02 in. lb. from said proximal end portion to said distal end of the grasping member.

51. An apparatus as recited in claim 44, wherein said needle and said grasping member each comprising material from a group consisting of: nickel titanium alloy, nickel, titanium, stainless steel and surgical steel.

52. An apparatus as recited in claim 43, wherein said grasping member is selectively advanceable and retractable relative to said pre-tied knot and said distal end portion of said needle.

53. An apparatus as recited in claim 43, further comprising:
   a first member located adjacent to said distal end of the needle, wherein said first member, said suture needle and said grasping member are disposed to permit selective relative movement therebetween, and wherein said first member is positionable to engage said suture material to position a pre-tied knot thereof beyond said distal end of the needle.

54. An apparatus as recited in claim 53, further comprising:
   a handle slideably interconnected with a proximal end portion of said grasping member and fixedly interconnected with a proximal end portion of said needle.

55. An apparatus as recited in claim 53, further comprising:
   a second member having a distal surface adapted for cutting said suture material, wherein said second member and at least one of said first member and said needle are disposed to permit selective relative movement between.

56. An apparatus as recited in claim 40, wherein said grasping member is selectively advanceable and retractable relative to said pre-tied knot.

57. An apparatus as recited in claim 40, wherein said pre-tied knot is concentrically disposed about said grasping member.

58. An apparatus as recited in claim 40, further comprising:
   a first member for selectively advancing said pre-tied knot relative to said grasping member.

59. An apparatus as recited in claim 40, wherein said suture needle comprises:
   an arcuate piercing tip.

60. A method for suturing comprising:
   disposing a pre-tied knot of a suture material about a needle and a grasping member;
   advancing a limited portion of said needle through a patient tissue site, wherein an end portion of said suture material is pulled through the patient tissue by the needle and protrudes from the patient tissue;
   manipulating said grasping member to grasp said protruding end portion of said suture material;
   passing said grasped end portion of said suture material through said pre-tied knot; and,
   positioning said pre-tied knot beyond said needle and said grasping member at said patient tissue site.

61. A method as recited in claim 60, further comprising:
   retaining said end portion of the suture material at a distal end of said needle prior to said advancing step.

62. A method as recited in claim 61, wherein said retaining step includes:
   grasping said end portion of said suture material with said grasping member; and,
   pulling said grasped end portion of said suture material into a hollow piercing tip at said distal end of the needle.

63. A method as recited in claim 61, further comprising:
   releasing said end portion of the suture material from said distal end of the needle after said advancing step; and,
   withdrawing said limited portion of the needle from the patient tissue site after said releasing step.

64. A method as recited in claim 61, wherein said manipulating step includes:
   advancing said grasping member relative to said pre-tied knot.

65. A method as recited in claim 64, wherein said manipulating step includes:
   locating said end portion of the suture material through a loop defined by said grasping member.

66. A method as recited in claim 65, wherein said passing step includes:
   retracting said grasping member relative to said pre-tied knot.

67. A method as recited in claim 60, wherein said positioning step includes:
   advancing a pusher member, disposed concentrically about said grasping member, to engage said pre-tied knot.

68. A method as recited in claim 67, wherein said needle, grasping member and pusher member are interconnected in a surgical instrument, and wherein the method further comprises:

inserting said surgical instrument through a tubular member having a distal end adjacent to said patient tissue site; and externally manipulating said surgical instrument to complete each of said retaining, advancing, releasing, withdrawing, grasping and positioning steps.

69. A method as recited in claim 68, further comprising:

imaging each of said retaining, advancing, releasing, withdrawing, grasping and positioning steps at said distal end of said tubular member.

* * * * *